April 14, 1964 O. O. DUNHAM Plant Pat. 2,389
CHRYSANTHEMUM PLANT
Filed Sept. 7, 1962
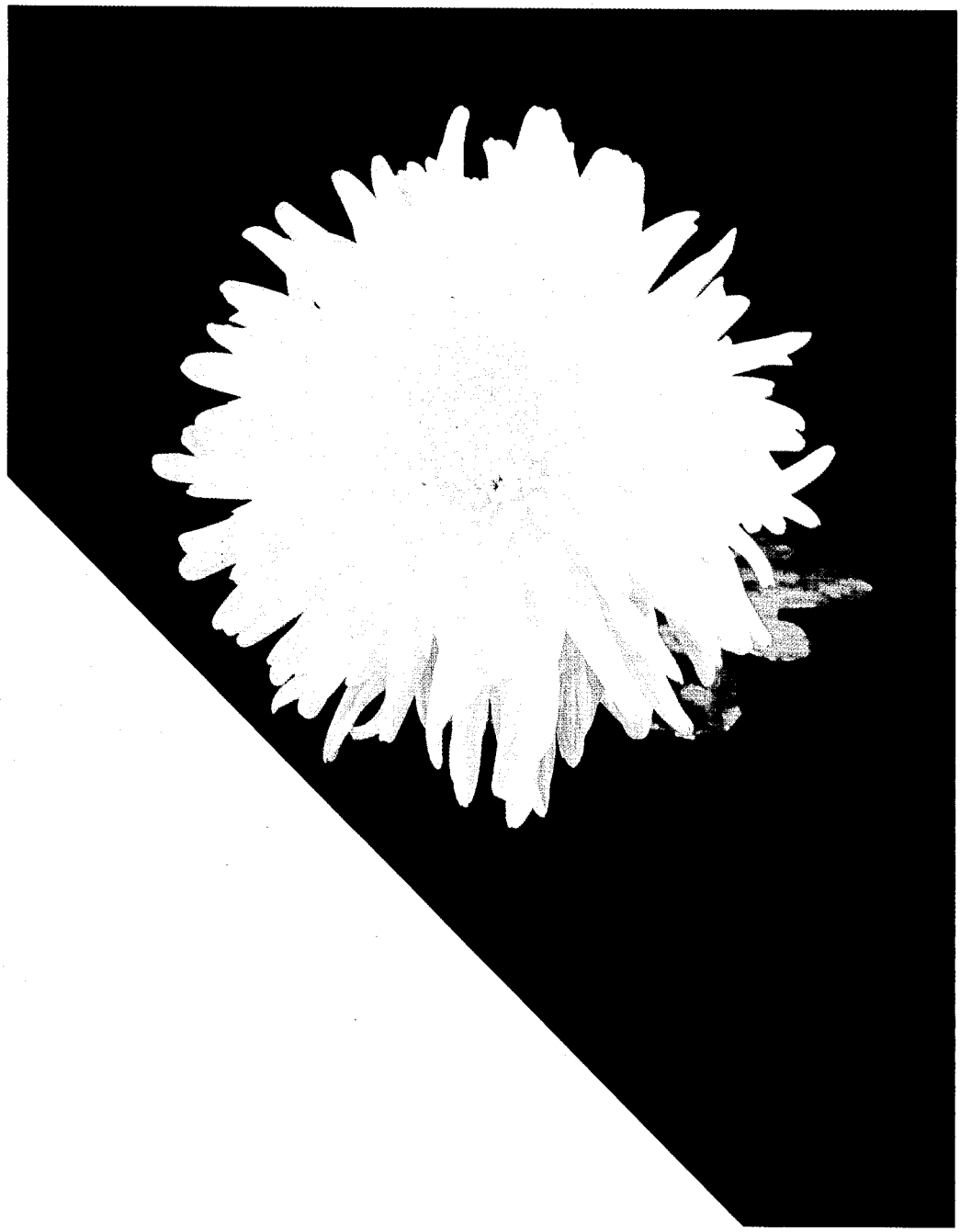
Inventor
O. O. Dunham
by Robb & Robb
attorneys United States Patent Office Plant Pat. 2,389
Patented Apr. 14, 1964

2,389
CHRYSANTHEMUM PLANT

Orville O. Dunham, Niles, Mich., assignor to George J. Ball, Inc., West Chicago, Ill., a corporation of Illinois Filed Sept. 7, 1962, Ser. No. 222,250
1 Claim. (Cl. Plt.—77)

My present invention comprises a new and distinct variety of chrysanthemum plant which is the result of crossing the variety which I designate as "#5350," an unpatented variety of my own introduction with another variety of my own introduction, likewise unpatented and which I designate as "Gorgeous."

The principal object of this invention has been to produce a new variety of chrysanthemum plant of the *indicum* type which provides a flower of more decorative and less reflexing appearance than the parents, with a good flower color and the tendency to retain its freshness for a longer period of time than the parents, further providing early and continuous blooming as a desirable attribute thereof.

Over the course of many years I have carried out an intensive program of development of chrysanthemums of various types and the present new variety is one of the results thereof, requiring careful selection and cross breeding of various plants.

The result of the specific hybridization previously referred to has been to produce my present new and distinct variety of chrysanthemum characterized by the more decorative, less reflexing bloom, longer lasting, more fresh retaining appearance of the blooms with a color of attractive nature ranging from a brilliant yellow center to white extremity at the edges of the bloom.

My new variety derives a number of characteristics from both parents, but better characteristics than either separately and my new variety differs from both of its parents and from other known varieties in many respects.

My new variety may be compared to a known garden mum variety "Genista," an unpatented variety of unknown origination, and in such comparison it flowers earlier than Genista, the flowers are more attractive and color is much better. Further my new variety makes a desirable spring pot plant in flower whereas Genista cannot be used for this purpose since it does not respond as evenly as my new variety. My new variety is more compact in growth than Genista.

Specifically the blooms of my new variety are of a brilliant yellow to white color (Nickerson Color Fan published by The Munsell Color Company), the blooms having the brighter outer color with the brilliant yellow center. As grown in the vicinity of Niles, Michigan, in uniform culture, plants of my new variety have grown to an average height of 16 inches.

My new variety is somewhat affected by hot and wet weather which cause the petals of the blooms to burn and rot respectively under the worst conditions but generally the blooms are of such a nature as to retain good flower color throughout the life of the bloom and the fresh appearance previously mentioned.

Under the conditions of culture previously mentioned, which have been undertaken in the region of Niles, Michigan, plants of my new variety grow very vigorously, somewhat more compact than other known varieties.

My new variety when grown in the region of Niles, Michigan, blooms from early September continuously until a killing frost, the blooms being of medium size and profusely in clusters on each plant.

My new variety has been asexually reproduced by cuttings in the vicinity of Niles, Michigan, the observations made and forming a basis for the color and other characteristic definitions having taken place in mid-October.

My new variety has been found to retain its distinctive characteristics through successive asexual reproduction.

The accompanying drawing forming a part hereof shows a typical plant of my new variety of chrysanthemum.

The following is a detailed description of my new variety of chrysanthemum plant, the color references being to the Nickerson Color Fan published by The Munsell Color Company:

*Description*

Parentage: Seedling.
- *Seed parent.*—"#5350" (unpatented).
- *Pollen parent.*—"Gorgeous" (unpatented).

Classification: Botanic—*Chrysanthemum indicum*

*Flower*

Blooming habit: Blooms profusely and continuously from early September until a killing frost.
- Observations were made in the vicinity of Niles, Michigan, during mid-October.

Bud:
- *Size.*—Large.
- *Form.*—Short with flat top.
- The petals burn in wet weather but not very markedly affected by hot weather.

Color:
- *When sepals first divide.*—7.5Y–9/8.
- *When petals begin to unfurl.*—7.5Y–9/8.
- *When half blown.*—Inside of petals: 5Y–9/9. Reverse of petals: White.
- *Sepals.*—Smooth edge.
- *Calyx.*—Shape—funnel. Size—large and broad. Aspect—smooth. No odor when rubbed.
- *Peduncle.* — Length — short. Aspect — smooth. Strength—stiff. Bud opens well.

Bloom:
- *Size.*—Medium. Average size when fully expanded about 4½".
- *Borne.*—In clusters and irregular.
- *Stems.*—Medium, strong.
- *Form.*—When first open—flat. Permanence—retains its form to the end. Fashion—like a show dahlia.
- *Petalage.*—Very double, many petals and stamens hidden. Number of petals—too numerous to count.
- *Color.*—Center of flower—5Y–9/9. Outer petals—White washed with 5Y–9/9. Base of petals (singlet)—10Y–9/9. Inside of petals—White washed with 5Y–9/9. Reverse of petals—White. General tonality from a distance—5Y–9/9.
- *Discoloration.*—General tonality at end of—First day: 5Y–9/9. Second day: retains the same 5Y–9/9. Third day: color maintained well throughout the aging, substantially the same 5Y–9/9.

Petals:
- *Texture.*—Thick. Somewhat affected by hot weather in that they burn and wet weather tends to rot.
- *Appearance.*—Inside—shiny. Outside—shiny.
- *Form.*—Flat.
- *Arrangement.*—Imbricated.
- *Petaloids in Center.*—Many.
- *Persistence.*—Hang on and dry.
- *Fragrance.*—None.
- *Lastingness.*—On the plant—very long. Cut flower—very long.

Genital organs:
- *Stamens, anthers.*—Small, many. Arrangement—regular around styles.
- *Stamens, filaments.*—Short.
- *Styles.*—Columnar and short.
- *Ovaries.*—Protruding from calyx.

Fruit: Variety is fertile with its own pollen.
*Form.*—Seeds protruding.
*Aspect.*—Rough and hairy.
*Sepals.*—Recurved.

Plant:
*Form.*—Bush.
*Growth.*—Medium and branching.
*Height.*—Approximately 16″ average.
*Spread.*—Approximately 16″.

Foliage:
*Leaflets.*—Single leaves.
*Size.*—Medium.
*Quantity.*—Normal.
*Color.*—Upper side—10GY–4/5. Under side—7.5GY–5/7.

*Texture.*—Upper side—glossy.
*Ribs and veins.*—Ordinary.
*Edge.*—Undulated.
*Under side.*—Smooth.
*Stipules.*—Short and smooth.

I claim:

A new and distinct variety of chrysanthemum plant substantially as herein disclosed, characterized as to novelty by its more decorative, less reflexing blooms, the longer lasting more fresh retaining appearance of the blooms, the brilliant yellow center to white extremity of the blooms, the branching form of its plant, and its early profuse and continuous, long blooming habit.

No references cited.